United States Patent [19]

Demosthene et al.

[11] 4,266,058
[45] May 5, 1981

[54] SYNTHESIS OF 2-ISOPROPYLAMINO-PYRIMIDINE

[75] Inventors: Claude G. Demosthene, Aramon; Christian R. Aspisi, Boulbon, both of France

[73] Assignee: Societe d'Etudes de Produits Chimiques, Paris, France

[21] Appl. No.: 162,114

[22] Filed: Jun. 23, 1980

[30] Foreign Application Priority Data

Jul. 4, 1979 [GB] United Kingdom ............... 23224/79

[51] Int. Cl.³ ........................................... C07D 239/42
[52] U.S. Cl. ..................................... 544/330; 544/318
[58] Field of Search .......................................... 544/330

[56] References Cited

U.S. PATENT DOCUMENTS

| 2,586,844 | 2/1952 | McKay et al. | 544/330 |
| 4,116,674 | 9/1978 | Sunley et al. | 544/330 |

OTHER PUBLICATIONS

Brown, *The Pyrimidines*, pub. by Interscience (1962), pp. 298–300.

*Primary Examiner*—Paul M. Coughlan, Jr.
*Attorney, Agent, or Firm*—Eyre, Mann, Lucas & Just

[57] ABSTRACT

The present invention provides a process for the synthesis of 2-isopropylamino-pyrimidine by aminolysis of 2-methylsulphonyl-pyrimidine using isopropylamine. The aminolysis is effected, according to the present invention, by refluxing isopropylamine and 2-methylsulphonyl-pyrimidine in the absence of a solvent. Using this technique, the 2-isopropylamino-pyrimidine has been obtained in a substantially quantitative yield.

1 Claim, No Drawings

SYNTHESIS OF 2-ISOPROPYLAMINO-PYRIMIDINE

Several syntheses have been proposed for 2-isopropylamino-pyramidine. These include the aminolysis of 2-chloropyrimidine with isopropylamine, and the cyclization of N-isorporylguanidine with 1,1,3,3-tetraethoxypropane.

It has been described in Eurpoean Patent Application No. 79400393.9 filed on June 15, 1979 the synthesis of 2-isopropylamino-pyrimidine by the action of an alkali borohydride and a carboxylic acid on 2-aminopyrimidine in the presence of acetone.

The present invention provides a process for the synthesis of 2-isopropylamino-pyrimidine by aminolysis of 2-methylsulphonyl-pyrimidine using isopropylamine. The aminolysis is effected, according to the present invention, by refluxing isopropylamine and 2-methylsulphonyl-pyrimidine in the absence of a solvent. Using this technique, the 2-isopropylamino-pyrimidine has been obtained in a substantially quantitative yield.

The synthesis of the starting material, 2-methulsulphonyl-pyrimidine, is described by Brown D. J. & Ford P. W. (J. Chem. Soc (c) 1967 568) with 50% yield starting from 2-methylthio-pyrimidine. The technique described by Brown and Ford comprises bubbling chlorine through an aqueous suspension of 2-methylthio-pyrimidine at from 0° C. to +5°0 C.

This technique has been improved by passing the chlorine more slowly and reducing the reaction temperature to from −5° C. to 0° C. It has thus been obtained a yield of approx 90%.

The preparation of 2-methylthio-pyrimidine was first described by Boarland M. P. V. and McOmie J. P. W. (J. Chem. Soc. 1952, 3716) with a yield of 62% starting from 2-mercapto-pyrimidine and methyl sulphate. Hunig S. and Oette K. F. (Liebig's Annalen der Chemie, 1961, 640, 98) obtained a yield of 83%.

The phase transfer catalysis technique of Dou, H. et al. (Phosphorus and Sulphur and the related elements, 1977, 3, 355) was applied to obtain the 2-methylthio-pyrimidine in quantitative yield.

The following reaction scheme illustrates the synthesis starting from 2-mercapto-pyrimidine.

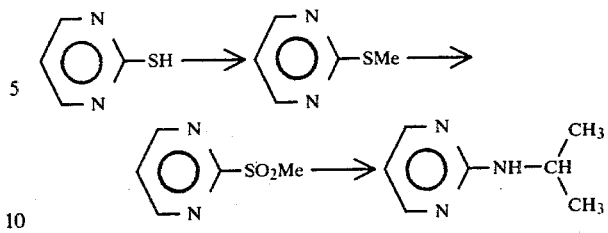

The following example illustrates the present improvement in the process.

EXAMPLE (a) Synthesis of 2-methylsulphonyl-pyrimidine

Into a 200 ml. reactor, there were introduced 10 g. (0.0794 mole) 2-methylthiopyrimidine and 100 ml. water.

Chlorine was bubbled through slowly at slightly below 0° C. After 5 minutes, there was obtained a solution. Chlorine passage was continued, slowly, for 1 hour whiling maintaining the same temperature. During this time, the progress of the reaction was confirmed by thin layer chromatography. The chlorine supply was then interrupted. The flask was shaken for 1 extra hour at 0° C. The pH was adjusted to 8 using $K_2CO_3$. Extraction was with a chlorinated solvent. The organic phase was dried using $Na_2SO_4$, and the solvent was then evaporated off.

There was obtained a white product which was recrystallized twice from ethanol.

Yield 11.3 g: 90%. MP 70.72° C. (lit 73°–74° C.).

(b) Synthesis of 2-isopropylamino-pyrimidine 2 g. (0.0126 mole) of 2-methysulphonly-pyrimidine were suspended in 20 ml isopropylamine.

Refluxing was carried out, rapidly obtaining a solution. After 1 hour (the progress of the reaction being confirmed by thin layer chromatography) the refluxing was stopped and excess isopropylamine was removed. There were added 100 ml water and the pH was adjusted to 9 using soda wash.

Extraction was with a chlorinated solvent. The organic phase was dried over $Na_2SO_4$ and the solvent was evaporated off.

There were obtained 1.7 g of product (∼100% yield).

The product could be used as such or in the form of its salts.

We claim:

1. Process for the synthesis of 2-isopropylamino-pyrimidine by aminolysis consisting in refluxing stoichiometric proportions of isopropylamine and 2-methysulphonyl-pyrimidine in the absence of a solvent.

* * * * *